US008550253B2

(12) United States Patent
Nakayama

(10) Patent No.: US 8,550,253 B2
(45) Date of Patent: Oct. 8, 2013

(54) FILTRATION APPARATUS

(75) Inventor: Daisuke Nakayama, Tokyo (JP)

(73) Assignee: Shimadzo Corporation, Kyoto (JP)

( * ) Notice: Subject to any disclaimer, the term of this patent is extended or adjusted under 35 U.S.C. 154(b) by 0 days.

(21) Appl. No.: 13/432,126

(22) Filed: Mar. 28, 2012

(65) Prior Publication Data

US 2012/0251412 A1    Oct. 4, 2012

(30) Foreign Application Priority Data

Apr. 4, 2011  (JP) ................................. 2011-082940

(51) Int. Cl.
*B01D 33/00* (2006.01)

(52) U.S. Cl.
USPC ............................ 210/391; 210/439; 210/636

(58) Field of Classification Search
USPC .......................................... 210/391, 439, 636
See application file for complete search history.

(56) References Cited

U.S. PATENT DOCUMENTS

2002/0050297 A1* 5/2002 Timney ...................... 137/625.5
2007/0095754 A1* 5/2007 Livingston et al. ........... 210/636

FOREIGN PATENT DOCUMENTS

JP    2009-142746 A    7/2009

* cited by examiner

*Primary Examiner* — Sally Merkling
(74) *Attorney, Agent, or Firm* — Westerman, Hattori, Daniels & Adrian, LLP

(57) ABSTRACT

A filtration apparatus includes: a filtration chamber; a sample introducing port for introducing a sample into the filtration chamber; a sample discharge port disposed at a position on an opposite side of the filtration chamber from the sample introducing port; a filtration filter provided in the filtration chamber to filter the sample introduced from the sample introducing port; and a filtrate discharge port for discharging filtrate which has passed through the filtration filter. The filtration filter is disposed such that its filter face is parallel to a flowing direction of the sample introduced from the sample introducing port when the sample discharge port is open. An opening and closing mechanism for opening and closing the sample discharge port is disposed between the filtration chamber and the sample discharge port.

13 Claims, 7 Drawing Sheets

FILTRATION APPARATUS

BACKGROUND OF THE INVENTION

1. Field of the Invention

The present invention relates to a filtration apparatus for filtering an analytical sample including suspended matter as pretreatment of the sample and for supplying the filtrate to an analyzing apparatus.

2. Description of the Related Art

A filtration apparatus is used to adjust a sample for analysis and, in particular, a slurry sample including suspended matter. FIG. 7 shows an example of a general filtration apparatus. This filtration apparatus includes a filtration device 30 having, inside itself, a space 34 which serves as a filtration chamber for filtering a sample. A flat filtration filter 32 partitioning the space 34 into two is provided at a center of the space 34 in the filtration device 30. A pipe 36 for introducing the sample is connected to one end of the filtration device 30 and a pipe 38 for discharging filtrate is connected to the other end. The pipes 36 and 38 communicate with each other through the space 34 in the filtration device 30 and the filter 32 is disposed to be perpendicular to a flowing direction of fluid between the pipe 36 and the pipe 38.

In such a filtration apparatus, the filtration filter 32 is clogged with suspended matter in the sample and a flow rate of the filtrate passing through the filtration filter 32 reduces with the passage of time since the starting of the filtration, and therefore, cleaning for unsticking the suspended matter accumulating on a surface of the filtration filter 32 needs to be carried out periodically. In this case, a method of cleaning is backward cleaning for introducing a cleaning solution or a cleaning gas from the pipe 38 into the filtration device 30 with the introduction of the sample from the pipe 36 stopped, unsticking the suspended matter stuck on the filtration filter 32, and discharging the suspended matter through the pipe 36.

As the filtration apparatus, there is an apparatus using a cylindrical disc filter besides the apparatus using the flat filtration filter. In such a filtration apparatus, it is necessary to carry out the backward cleaning using the cleaning solution or the cleaning gas in order to remove the suspended matter stuck on the surface of the disc filter.

The sample, however, cannot be filtered during the backward cleaning. In a case where the sample includes a large amount of suspended matter, the backward cleaning needs to be carried out frequently, and therefore, it is impossible to continuously supply the filtrate to the analyzing apparatus.

A method of cleaning the disc filter, therefore, which is different from the backward cleaning has been proposed (see Japanese Unexamined Patent Publication No. 2009-142746). The proposed filtration apparatus includes a filtration device housing, inside itself, a cylindrical disc filter. A sample introducing port (sample inlet) for introducing a sample is formed at a lower portion of the filtration device, and a sample discharge port (drain outlet) is formed at an upper portion of the filtration device. Part of the sample introduced from the sample introducing port passes through a clearance in the disc filter. At this time, the suspended matter included in the sample adheres to a surface of the disc filter and the filtrate which has passed through the disc filter passes through an inner flow path in the disc filter, and is introduced to a filtrate discharge port. The rest of the sample introduced from the sample introducing port passes by the disc filter and is discharged from the sample discharge port. At this time, the suspended matter stuck on an outer surface of the disc filter is unstuck by the sample flowing by the disc filter and is discharged from the sample discharge port together with the sample. Therefore, it is possible to remove the suspended matter stuck on the outer surface of the disc filter without carrying out the backward cleaning for causing the cleaning solution or the cleaning gas to flow from the inside toward the outside of the disc filter.

Although the suspended matter stuck on the outer peripheral portion of the disc filter can be removed by the sample flowing by the filter in the above structure, the suspended matter stuck on the inner side cannot be removed. Therefore, it is impossible to completely prevent occurrence of clogging of the disc filter and the filtration apparatus needs to be disassembled for maintenance of the disc filter, or the backward cleaning needs to be carried out periodically.

SUMMARY OF THE INVENTION

It is an object of the present invention to eliminate the need for maintenance of the filter by disassembling the filtration apparatus and the backward cleaning.

A filtration apparatus according to the present invention includes: a filtration chamber; a sample introducing port for introducing a sample into the filtration chamber; a filtration filter provided in the filtration chamber to filter the sample introduced from the sample introducing port; and a filtrate discharge port for discharging filtrate, which has passed through the filtration filter, from the filtration chamber. A sample discharge port is disposed at a position on an opposite side of the filtration chamber from the sample introducing port and an opening and closing mechanism for opening and closing the sample discharge port is provided between the filtration chamber and the sample discharge port. The filtration filter is disposed in such a way that its filter face is parallel to a flowing direction of the sample introduced from the sample introducing port when the sample discharge port is open.

In the filtration apparatus according to the present invention, when the opening and closing mechanism brings the sample discharge port into a closed state, filtration of the sample can be carried out. If the filtration of the sample is carried out with the sample discharge port closed by the opening and closing mechanism, an amount of suspended matter accumulating on the surface of the filtration filter increases with the passage of time, the filtration filter is clogged, and an amount of the sample which can pass through the filtration filter reduces. In this case, by opening the opening and closing mechanism, the sample passes on the surface of the filtration filter to unstick the suspended matter accumulating on the surface of the filtration filter and the suspended matter is discharged from the sample discharge port together with the sample. In this way, it is possible to remove the suspended matter accumulating on the surface of the filtration filter without carrying out the backward cleaning.

Opening and closing operations of the opening and closing mechanism may be carried out manually or a control section implemented by a data processing computer for automatically controlling the opening and closing operations of the opening and closing mechanism may be provided.

If the clogging of the filtration filter proceeds, pressure in the filtration chamber increases. Therefore, it is preferable that the filtration apparatus further includes pressure detecting means for detecting pressure in the filtration chamber and, the control section for controlling the opening and closing operations of the opening and closing mechanism includes opening and closing means based on pressure and is formed to open the sample discharge port only when the pressure in the filtration chamber detected by the pressure detecting means exceeds a predetermined value. In this way, the sample discharge port is opened automatically and cleaning of the filtration filter is carried out when the suspended matter accumulates on the surface of the filtration filter to clog the filter.

The control section may include opening and closing means based on time and is formed to open the sample discharge port at certain time intervals. In this way, the pressure detecting means for detecting the pressure in the filtration chamber becomes unnecessary and the structure of the filtration apparatus becomes simple.

An amount of time for which the control section opens the sample discharge port is preferably a preset amount of time for removing the suspended matter accumulating on the surface of the filtration filter. In this way, after the suspended matter is removed, the sample discharge port is closed automatically, and the filtration of the sample is continued.

A state in which the sample discharge port is closed by the opening and closing means may not be a completely closed state but may be a state in which the sample discharge port is open to a degree necessary to adjust a flow rate of the filtrate passing through the filtration filter. In a case where a large amount of sample is introduced from the sample introducing port when the sample discharge port is closed completely, a load is applied on the filtration filter to reduce life of the filtration filter. Therefore, by keeping the sample discharge port slightly open in the case where the large amount of sample is introduced from the sample introducing port, it is possible to reduce the load applied on the filtration filter to thereby prevent reduction of the life of the filtration filter.

With the filtration apparatus according to the present invention, the sample discharge port is disposed at a position on the opposite side from the sample introducing port, the opening and closing mechanism for opening and closing the sample discharge port is provided, and the filtration filter is disposed in such a manner that its filter face is parallel to the flowing direction of the sample introduced from the sample introducing port when the sample discharge port is open. Therefore, by opening the sample discharge port by the opening and closing mechanism, the sample can flow on the surface of the filtration filter, and it is possible to remove the suspended matter accumulating on the surface of the filtration filter by utilizing the flow of the sample. Because the flat filtration filter is used, adhesion of the suspended matter to the inside of the filter as in the disc filter does not occur and cleaning operations other than the cleaning of the surface of the filtration filter by opening the opening and closing mechanism are unnecessary.

BRIEF DESCRIPTION OF THE DRAWINGS

FIGS. 2A and 2B are conceptual diagrams for explaining functions of the embodiment, wherein FIG. 2A shows a closed state of an opening and closing mechanism, and FIG. 2B shows an open state of the opening and closing mechanism, respectively;

FIGS. 4A and 4B are diagrams for explaining operations of the embodiment, wherein FIG. 4A is a flowchart and FIG. 4B is a graph showing an example of variation of pressure in a filtration chamber with time;

FIGS. 5A and 5B are schematic block sectional views showing an example of a structure of an opening and closing mechanism, wherein FIG. 5A shows an open state of the opening and closing mechanism and FIG. 5B shows a closed state of the opening and closing mechanism;

DETAILED DESCRIPTION OF THE INVENTION

Figure 1:
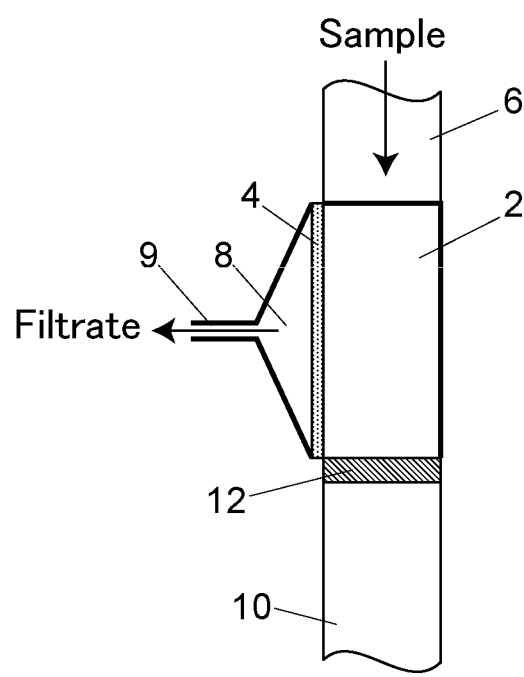
FIG. 1 is a conceptual diagram showing an embodiment of a filtration apparatus.

An embodiment of a filtration apparatus will be described with reference to a conceptual diagram in FIG. 1.

The filtration apparatus in the embodiment includes, inside itself, a filtration chamber 2. The filtration chamber 2 has a sample introducing port to which a sample supply flow path 6 is connected and a sample discharge port to which a drain flow path 10 is connected. A filtration filter 4 is provided between the sample introducing port and the sample discharge port. The filtration filter 4 is disposed in such a manner that a filter face is parallel to a flowing direction of a sample from the sample introducing port to the sample discharge port.

An opening and closing mechanism 12 is provided to the sample discharge port to open and close the port. The filtration chamber 2 is provided with a distributer 8 which is partitioned off by the filtration filter 4. The distributer 8 has a filtrate discharge port for discharging filtrate and a filtrate discharge flow path 9 is connected to the filtration discharge port.

Figure 2A:
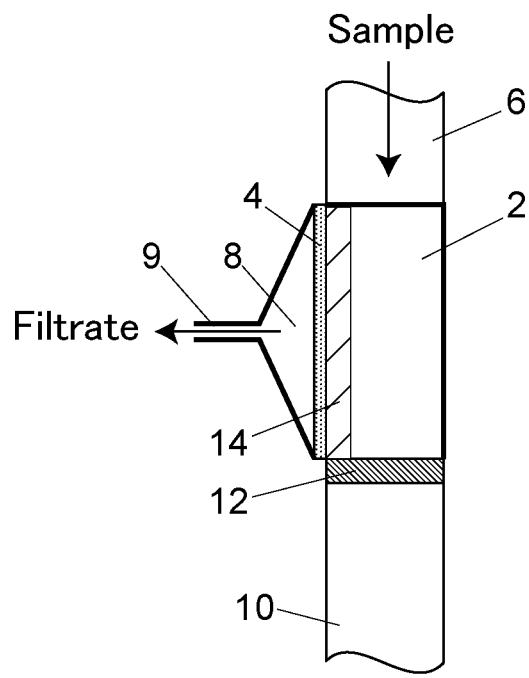
Figure 2B:
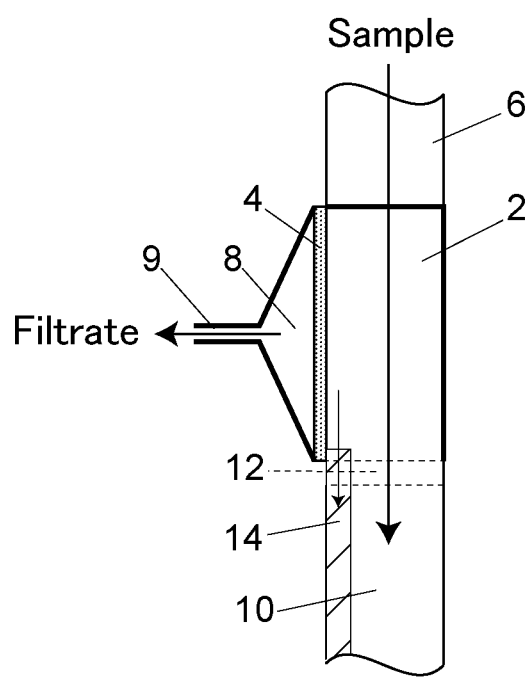

In this filtration apparatus, the opening and closing mechanism 12 is closed as shown in FIG. 2A to carry out filtration of the sample and is opened as shown in FIG. 2B to carry out cleaning of the filtration filter 4. If the opening and closing mechanism 12 is closed, the sample supplied from the sample supply flow path 6 passes through the filtration filter 4 and flows into the filtrate discharge flow path 9. Suspended matter 14 included in the sample is trapped and accumulates on the surface of the filtration filter 4, and an amount of the accumulation increases with the passage of time. If the amount of the accumulation of the suspended matter 14 on the surface of the filtration filter 4 increases, the filtration filter 4 is clogged, and an amount of the sample which can pass through the filtration filter 4 decreases to reduce filtration efficiency.

When a certain amount of suspended matter has therefore accumulated on the surface of the filtration filter 4, the opening and closing mechanism 12 is opened. If the opening and closing mechanism 12 is opened, the sample supplied from the sample supply flow path 6 passes on the surface of the filtration filter 4 and flows into the sample discharge flow path 10. The suspended matter 14 accumulating on the surface of the filtration filter 4 is unstuck by the flowing sample and is discharged into the sample discharge flow path 10 together with the sample.

Figure 3A:
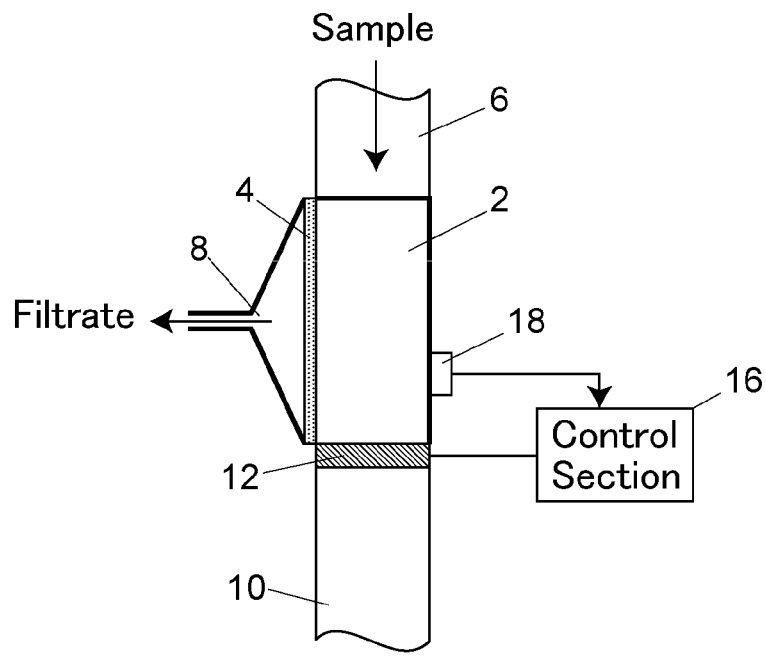
FIG. 3A is a conceptual diagram showing another embodiment.
Figure 3B:
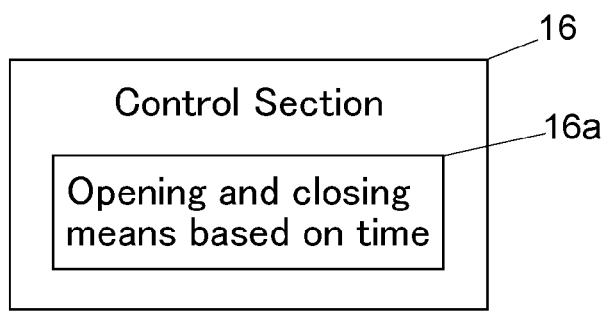
FIGS. 3B and 3C are block diagrams respectively showing functions of control sections.

The opening and closing mechanism 12 may be opened and closed manually at a proper time by an analyst or may be opened and closed automatically by providing a control section 16 for controlling the opening and closing mechanism 12 as shown in FIG. 3A.

The control section 16 may be implemented by a data processing computer. In this case, the data processing computer may be provided as a computer especially for this filtration apparatus or may be a computer for an analyzing apparatus provided with this filtration apparatus. The control section 16 may be implemented by a general-purpose personal computer.

The control section 16 may have, as a function of the computer, opening and closing means 16a based on time which is formed to open the opening and closing mechanism 12 for a certain amount of time at certain time intervals since the start of filtration of the sample. In this way, it is possible to clean the filtration filter 4 periodically without checking of the clogging of the filtration filter 4 by the analyst.

Figure 3C:
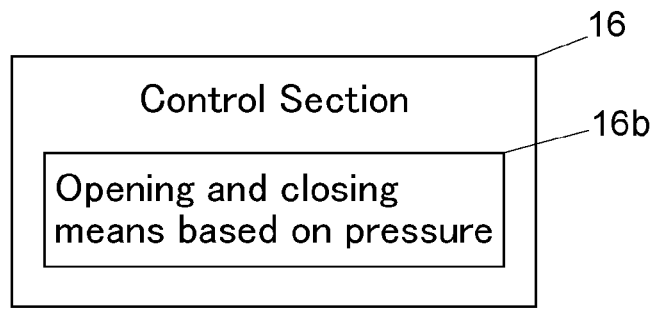

The clogging of the filtration filter 4 may be detected and the filtration filter 4 may be cleaned when the clogging is detected. FIGS. 3A and 3C show such an embodiment. In this embodiment, a pressure sensor 18 for detecting pressure in the filtration chamber 2 is mounted. The control section 16 for controlling the opening and closing mechanism 12 has, as a function of the computer, opening and closing means 16b based on pressure and for controlling the opening and closing mechanism 12 based on a detection signal from the pressure sensor 18.

Figure 4A:
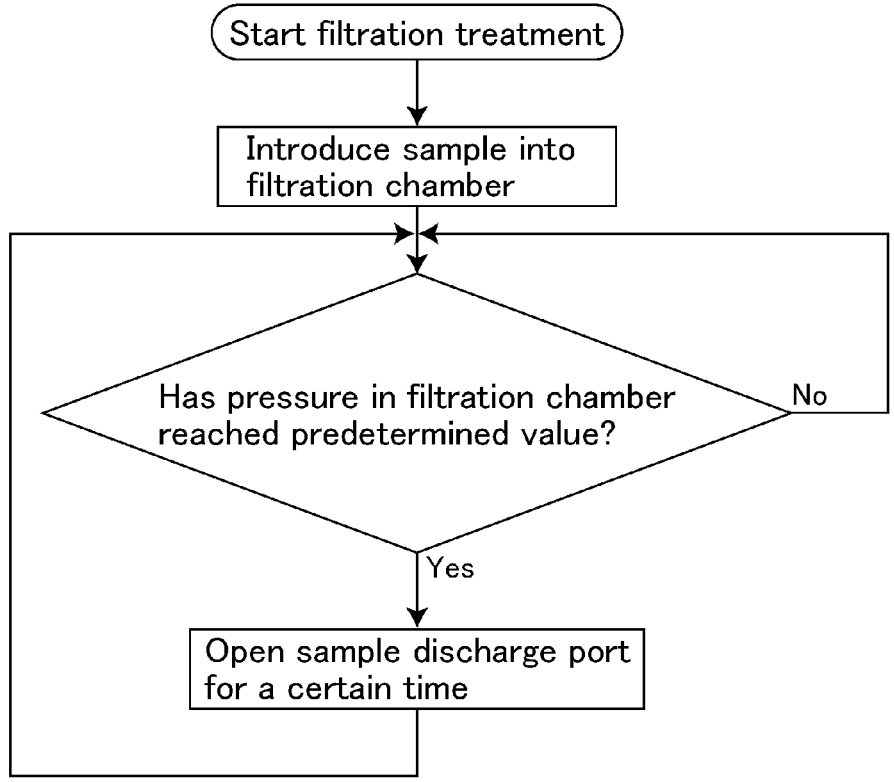

Operation of the filtration apparatus in the embodiment in FIGS. 3A and 3C will be described with reference to FIG. 4A. Filtration treatment of the sample is carried out by introducing the sample into the filtration chamber 2. In filtering the sample, the opening and closing mechanism 12 is closed, the sample passes through the filtration filter 4, and is introduced to the analyzing apparatus through the filtrate discharge flow path 9. The suspended matter included in the sample is trapped and accumulates on the surface of the filtration filter 4, and an amount of the accumulation increases with the passage of time. Because it becomes difficult for the sample to pass through the filtration filter 4 as the amount of the accumulation of the suspended matter on the surface of the filtration filter 4 increases, the pressure in the filtration chamber 2 increases gradually.

Figure 4B:
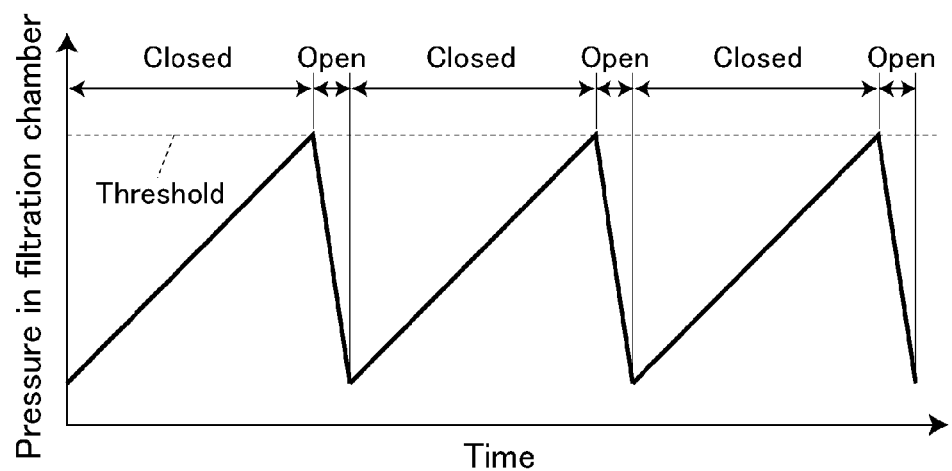

The opening and closing means of the control section 16 based on the pressure is formed to open the sample discharge port for a certain amount of time by means of the opening and closing mechanism 12 when the pressure in the filtration chamber 2 reaches predetermined pressure set in advance. Then, after opening the sample discharge port for the certain amount of time, the opening and closing means closes the sample discharge port again. In the filtration chamber 2, the pressure repeatedly increases and decreases as shown in FIG. 4B as the opening and closing mechanism 12 carries out the opening and closing operations.

Figure 5A:
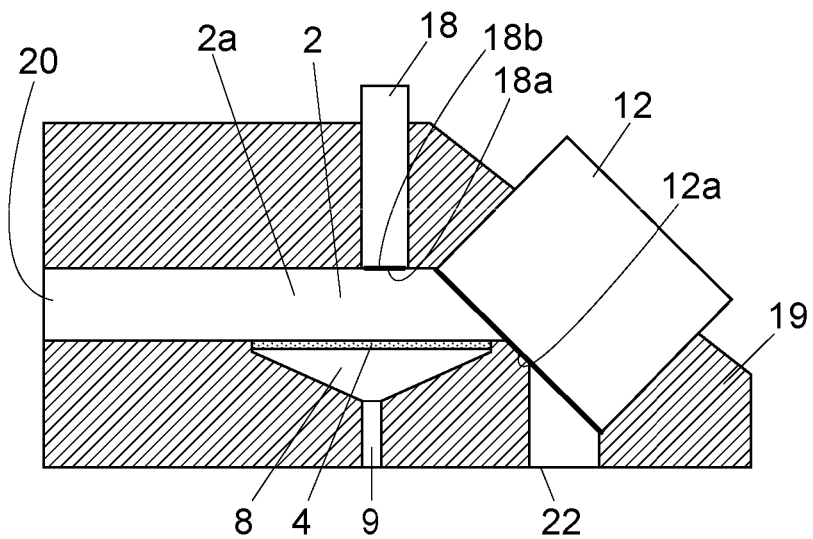
Figure 5B:
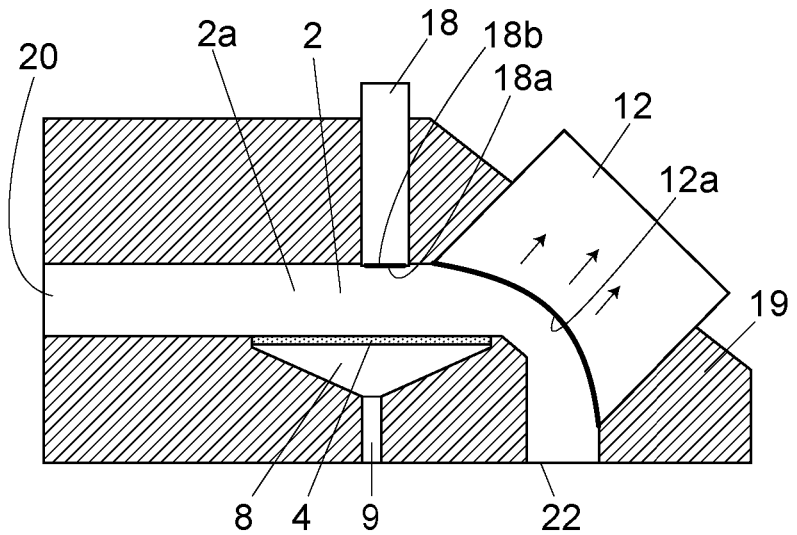

An example of a specific structure of the filtration apparatus in the embodiment in FIGS. 3A and 3C is shown in FIGS. 5A and 5B. FIGS. 5A and 5B show a sectional structure of a filtration device forming the filtration apparatus. A flow path 2a through which the sample flows is provided in a filtration device 19 and the filtration chamber 2 for filtering the sample is formed as part of the flow path 2a. One end 20 of the flow path 2a communicates with one side face of the filtration device 19 and the other end 22 communicates with a side face of the filtration device 19, adjacent to the side face communicating with the one end 20. Although it is not shown in the drawings, the sample supply flow path is connected to the one end 20 of the flow path 2a, and the sample discharge flow path is connected to the other end 22. The one end 20 of the flow path 2a serves as a sample introducing port, and the other end 22 serves as a sample discharge port.

The flow path 2a is bent at a right angle near and on a downstream side of the filtration chamber 2. The filtration filter 4 is provided to an inner wall of a portion of the flow path 2a which is on an upstream side of the bent portion and which serves as the filtration chamber 2. The filtration filter 4 is disposed parallel to a flowing direction of the sample introduced from the one end 20. The distributer 8 formed by a hollow portion is provided on an opposite side of the filtration filter 4 from the flow path 2a, and the filtrate discharge flow path 9 communicating with the outside of the filtration device 19 is provided to a bottom portion of the distributer 8. The filtrate discharge flow path 9 is connected to the analyzing apparatus.

The filtration device 19 includes a flow rate control valve 12 as the opening and closing mechanism for controlling a flow rate in the flow path 2a at the bent portion of the flow path 2a, and the pressure sensor 18 for detecting the pressure in the flow path 2a. The flow rate control valve 12 in this example includes a diaphragm 12a forming part of a wall face of a recessed portion of the bent portion of the flow path 2a. By driving the diaphragm 12a, the diaphragm 12a is brought into contact with a protruding portion facing the recessed portion of the bent portion of the flow path 2a to thereby close the flow path 2a (as in the state in FIG. 5A), and the diaphragm 12a is separated from the protruding portion to thereby open the flow path 2a (as in the state in FIG. 5B).

As the pressure sensor 18, a strain gauge pressure sensor is used. The pressure sensor 18 has a metal diaphragm 18a at its tip end and a resistance bridge 18b is stuck on a back face of the metal diaphragm 18a. The metal diaphragm 18a faces the flow path 2a and is strained due to increase of the pressure in the flow path 2a and resistance of the resistance bridge 18b changes according to an amount of the strain. Based on the resistance of the resistance bridge 18b, it is possible to detect the pressure in the flow path 2a.

Although the flow rate control valve 12 for opening and closing the flow path 2a by driving of the diaphragm 12a by utilizing the bent portion of the flow path is shown in the embodiment in FIGS. 5A and 5B, the flow rate control valve 12 is not limited to the valve provided to the bent portion of the flow path.

Figure 6A:
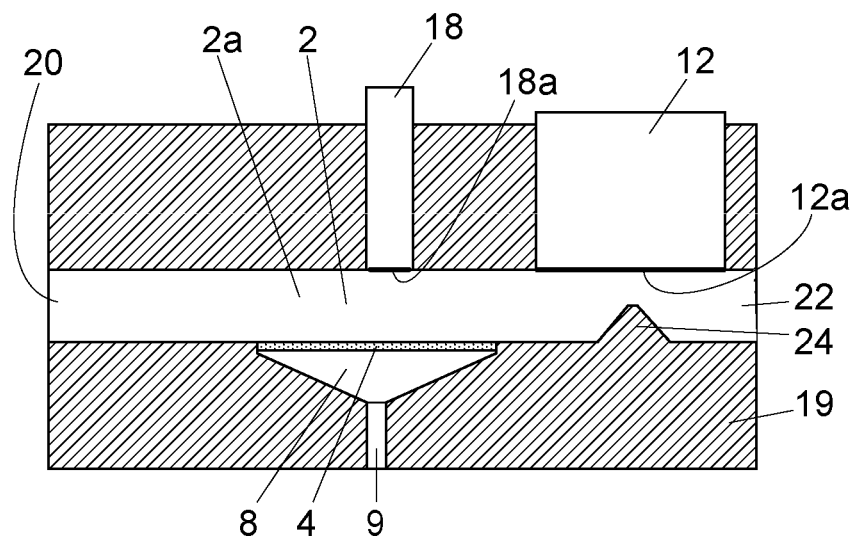
FIGS. 6A and 6B are schematic block sectional views respectively showing another example of the structure of the opening and closing mechanism.

Another example of the opening and closing mechanism is shown in FIG. 6A. In the opening and closing mechanism in FIG. 6A, a protrusion 24 is provided to a wall face of the flow path 2a which is near and on a downstream side of the filtration chamber 2 and the flow rate control valve 12 having the diaphragm 12a is provided to the flow path wall face at a position facing the protrusion 24. The protrusion 24 and the flow rate control valve 12 form the opening and closing mechanism. Further in the opening and closing mechanism, by driving the diaphragm 12a, the diaphragm 12a is brought into contact with the protrusion 24 to thereby close the flow path 2a and the diaphragm 12a is separated from the protrusion 24 to thereby open the flow path 2a.

Figure 6B:
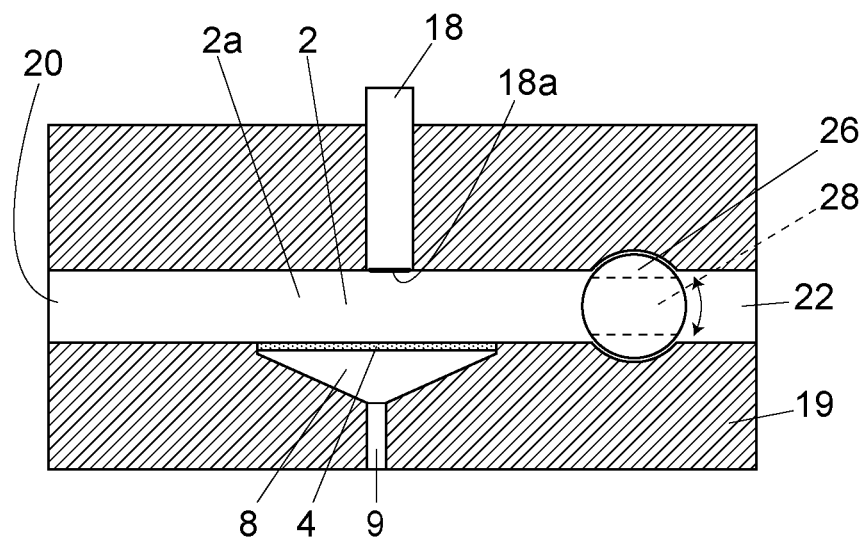
Figure 7:
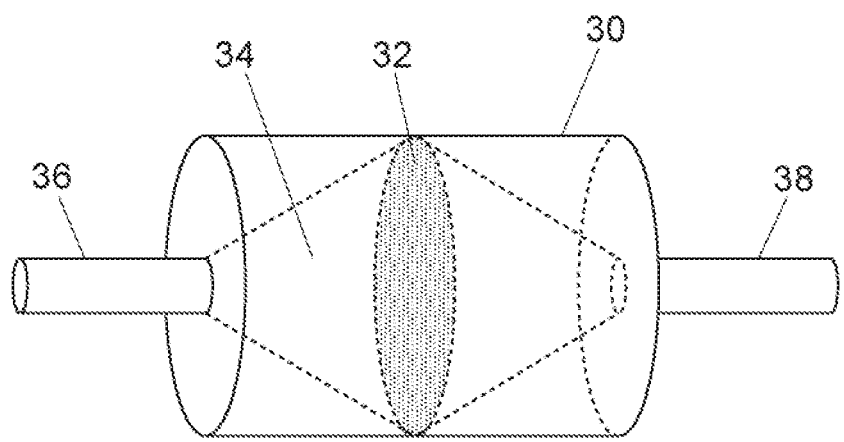
FIG. 7 is a perspective view showing an example of a conventional filtration apparatus.

Yet another example of the opening and closing mechanism is shown in FIG. 6B. In the opening and closing mechanism in FIG. 6B, a ball valve as a substitute for the diaphragm is mounted into the flow path 2a. In the opening and closing mechanism in FIG. 6B, a ball 26 having a through hole 28 is disposed as the ball valve in the flow path 2a at a position of the flow rate control valve 12 in the opening and closing mechanism in FIG. 6A. By driving the ball 26 for rotation from outside the flow path 2a, it is possible to switch between a state in which the through hole 28 opens the flow path 2a and a state in which the through hole 28 is at such a position as not to open the flow path 2a to thereby close the flow path 2a.

The invention claimed is:

1. A filtration apparatus comprising:
    a filtration chamber;
    a sample introducing port configured to introduce a sample into the filtration chamber;
    a sample discharge port disposed at a position on an opposite side of the filtration chamber from the sample introducing port;
    an opening and closing mechanism disposed between the filtration chamber and the sample discharge port configured to open and close the sample discharge port;

a filtration filter provided in the filtration chamber and configured to filter the sample introduced from the sample introducing port, the filter being disposed in such a way that its filter face is parallel to a flowing direction of the sample introduced from the sample introducing port when the sample discharge port is open; and a filtrate discharge port configured to discharge filtrate which has passed through the filtration filter.

2. A filtration apparatus according to claim 1, wherein the opening and closing mechanism is disposed in a flow path extending from the filtration chamber to the sample discharge port and is configured to open and close the flow path to thereby open and close the sample discharge port.

3. A filtration apparatus according to claim 2, wherein the flow path is bent at a right angle on a downstream side of the filtration chamber and the opening and closing mechanism is provided to the bent portion.

4. A filtration apparatus according to claim 3, wherein the opening and closing mechanism is a flow rate control valve including a diaphragm forming part of a wall face of a recessed portion of the bent portion of the flow path, and is configured to close the flow path by bringing the diaphragm into contact with a protruding portion facing the recessed portion of the bent portion of the flow path and to open the flow path by separating the diaphragm from the protruding portion.

5. A filtration apparatus according to claim 2, wherein the opening and closing mechanism includes a protrusion provided to a wall face of the flow path and a flow rate control valve having a diaphragm on a wall face of the flow path at a position facing the protrusion, and is configured to close the flow path by bringing the diaphragm into contact with the protrusion and to open the flow path by separating the diaphragm from the protrusion.

6. A filtration apparatus according to claim 2, wherein the opening and closing mechanism is a ball valve including a ball which has a through hole and is disposed in the flow path, and the opening and closing mechanism is configured to drive the ball for rotation from outside the flow path to thereby switch between a state in which the through hole opens the flow path and a state in which the through hole is at such a position as not to open the flow path to thereby close the flow path.

7. A filtration apparatus according to claim 1, further comprising:

a control section implemented by a data processing computer for automatically controlling opening and closing operations of the opening and closing mechanism.

8. A filtration apparatus according to claim 7, further comprising:

pressure detecting means for detecting pressure in the filtration chamber, wherein in order to automatically control the opening and closing operations of the opening and closing mechanism, the control section includes opening and closing means based on pressure, the opening and closing means controlling the opening and closing operations of the opening and closing mechanism in such a manner as to open the sample discharge port only when the pressure in the filtration chamber detected by the pressure detecting means exceeds a predetermined value.

9. A filtration apparatus according to claim 8, wherein the opening and closing means controls the opening and closing operations of the opening and closing mechanism in such a manner as to open the sample discharge port for a certain amount of time when the pressure in the filtration chamber exceeds a predetermined value.

10. A filtration apparatus according to claim 8, wherein the pressure detecting means is a strain gauge pressure sensor.

11. A filtration apparatus according to claim 7, wherein in order to automatically control the opening and closing operations of the opening and closing mechanism, the control section includes opening and closing means based on time, the opening and closing means controlling the opening and closing operations of the opening and closing mechanism in such a manner as to open the sample discharge port at certain time intervals.

12. A filtration apparatus according to claim 11, wherein the amount of time for which the opening and closing means opens the sample discharge port is a preset amount of time for removing suspended matter accumulating on a surface of the filtration filter.

13. A filtration apparatus according to claim 1, wherein the state in which the sample discharge port is closed by the opening and closing mechanism is not a completely closed state but is a state in which the sample discharge port is open to a degree necessary to adjust a flow rate of the filtrate passing through the filtration filter.

* * * * *